US008340917B2

(12) United States Patent
Banerjee et al.

(10) Patent No.: US 8,340,917 B2
(45) Date of Patent: Dec. 25, 2012

(54) SEQUENCE MATCHING ALLOWING FOR ERRORS

(75) Inventors: Jayanta Banerjee, Nashua, NH (US); Seema Sundara, Nashua, NH (US)

(73) Assignee: Oracle International Corporation, Redwood Shores, CA (US)

( * ) Notice: Subject to any disclaimer, the term of this patent is extended or adjusted under 35 U.S.C. 154(b) by 319 days.

(21) Appl. No.: 12/634,118

(22) Filed: Dec. 9, 2009

(65) Prior Publication Data

US 2011/0136686 A1    Jun. 9, 2011

(51) Int. Cl.
*G01N 33/48* (2006.01)
*G06G 7/48* (2006.01)

(52) U.S. Cl. ............................. 702/19; 703/11

(58) Field of Classification Search ................. None
See application file for complete search history.

(56) References Cited

U.S. PATENT DOCUMENTS 7,617,235 B2    11/2009    Srinivasan et al.

OTHER PUBLICATIONS

Altschul et al. Basic local alignment search tool, J. Mol. Biol. 1990, Oct. 5, 215(3): 403-10.*

* cited by examiner

*Primary Examiner* — Larry D Riggs, II
(74) *Attorney, Agent, or Firm* — Kraguljac Law Group, LLC

(57) ABSTRACT

Systems, methods, and other embodiments associated with sequence matching with no more than a number E errors are disclosed. A test fragment to be located within a target sequence with at most a number E errors is received. The test fragment is broken into E+1 test sub-fragments. If one test sub-fragment is located within the target sequence with no errors; a determination is made as to whether the other test sub-fragments are located within the target sequence adjacent to the one test sub-fragment with a total of at most E errors. If the other test sub-fragments are located within the target sequence adjacent the one test sub-fragment with at most E errors, a location of the test fragment within the target sequence is returned.

20 Claims, 6 Drawing Sheets

SEQUENCE MATCHING ALLOWING FOR ERRORS

BACKGROUND

Research in many areas of biotechnology, such as drug discovery, disease analysis, and crop improvements, involves matching fragments of sequences that are generated from a sample, with long sequences that represent biological components. For example, the human genome is a double helix of sequences of nucleotides, where one sequence is a complement of the other. There are 4 nucleotides in DNA sequences, more in RNA and protein sequences. Each nucleotide in a DNA sequence is represented by a character from the alphabet {a,c,t,g}. Each strand of the double helix that constitutes the human genome is a sequence of more than 3 billion characters. The 2 strands are not independent. For each character position in one strand, there is a complementary character in the corresponding position of the second strand. The characters a and t are complements of one another, and the characters c and g are complements of one another. Each character is also called a base, hence a genomic sequence is often said to contain more than 3 billion base-pairs (a base and its complement).

An average laboratory test of a DNA sample takes hours to days, and typically generates over 100 million test fragments, each having a small number of letters, usually between 36 and 500 letters. Although test fragments are in the form of a single strand, a test fragment must be matched against both strands because it is unknown from which strand the test fragment originates. Typically, the test fragments are individually matched to selected chromosomes in a process that may take many hours or days.

Matching between the fragments and the chromosomes typically allows for 1 or 2 errors in the match, such as mismatched letters or surplus characters in the fragment, to account for experimental errors. Some algorithms that perform fragment matching while allowing for errors are called BLAST algorithms. BLAST algorithms utilize in-memory analysis and are computationally intensive. Thus, they are generally inadequate for the high numbers of fragments that are generated for matching.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
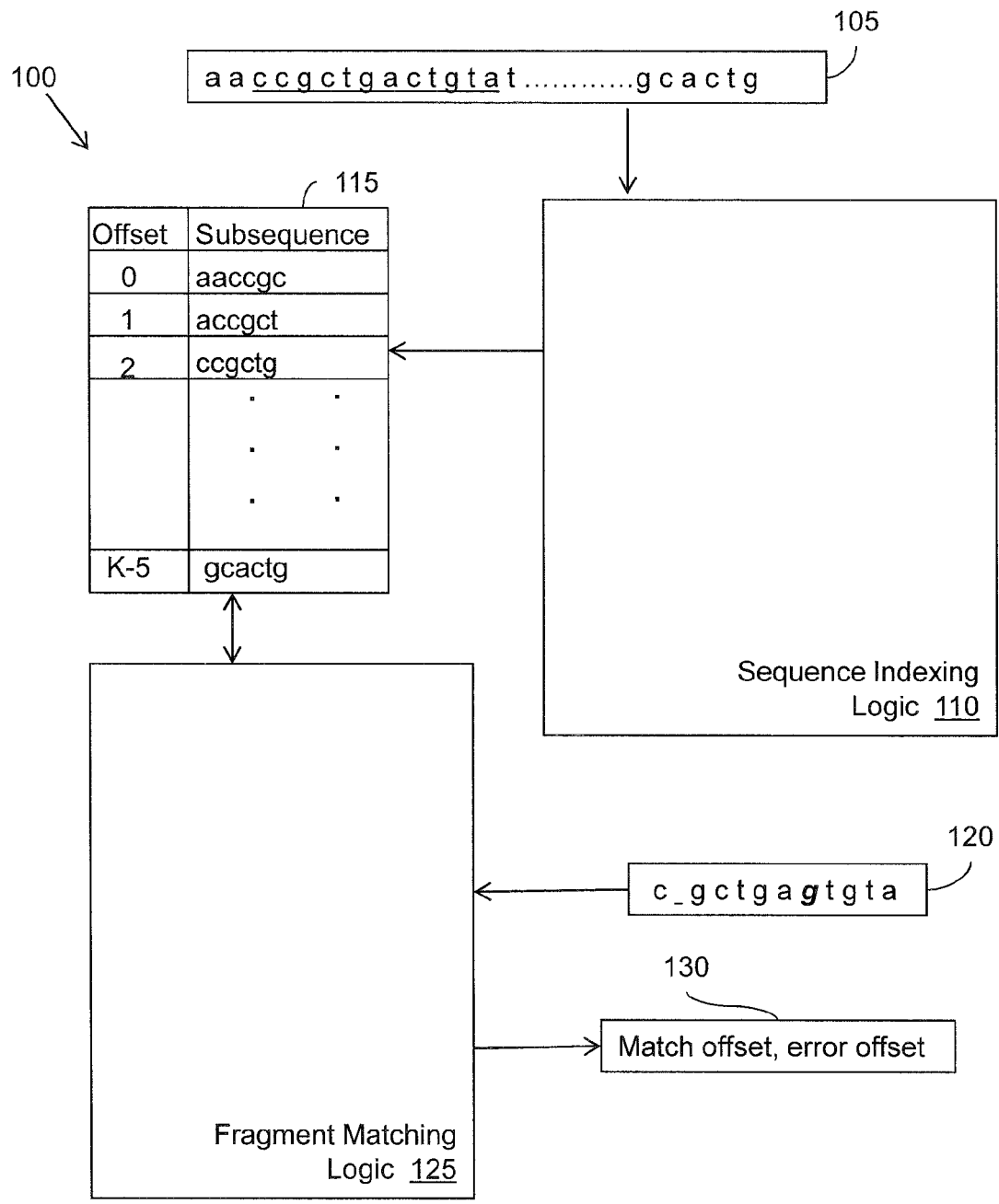
FIG. 1 illustrates an example embodiment of a system associated with sequence matching allowing for errors, where block 105 represents sequence identification number (seq. ID no.) 4, and where block 120 represents seq. ID no. 5.

Processing of genetic test samples typically involves generating a large number (over one hundred million) of genetic sequence fragments from a genetic test sample. These test fragments, typically between 36 and 500 characters in length, contain a string of characters taken from an alphabet that represents genetic components (nucleotides), such as {a,c,t,g} for chromosome data. RNA and protein sequences employ a larger alphabet of 5 and 20 characters, respectively. Often, the alphabet adds a character "n" that corresponds to a "not-sure" value, meaning that the particular character could not be determined.

The fragments are matched against genomic sequences that have been built in previous research. For the case of the human genome, various "builds" or combinations of 24 chromosomes have been generated and are stored persistently for comparison with test fragments from laboratory testing. Each chromosome is represented by a target sequence having between 50 million and 250 million characters. Test fragments are matched to the chromosome target sequence in an attempt to locate the test fragment within the chromosome sequence. Research in other biological areas such as plant development and drug discovery also involves matching test fragments from testing to a much larger target sequence representing pertinent genetic data.

Typically, a test fragment is deemed as matching a much larger target sequence when it can be located within the target sequence with 0, 1, or 2 errors. An error can be defined as a mismatch between characters in the test fragment and the corresponding character in the target sequence (this would include an "n" in the test fragment) or as a gap in the test fragment where no character is present in the target sequence, but a corresponding character is present in the test fragment (or vice versa).

The methods and systems described herein provide an effective way to locate a test fragment within a target sequence with no more than a number E errors. Each test fragment is broken into E+1 test sub-fragments. For example, if one error is allowed, the test fragment will be broken into 2 test sub-fragments. For each of these test sub-fragments, a determination is made as to whether the test sub-fragment is located in the target sequence with no errors. If none of the test sub-fragments is located in the target sequence with no errors, then the complete fragment must have at least E+1 (the number of test sub-fragments) errors. If this determination is made, no further matching needs to be done between the fragment and the target sequence. Thus, the vast majority of matching operations may be terminated after this first operation.

If it is determined that one of the test sub-fragments does indeed match with no errors, then a comparison of the other test sub-fragments to the portions of the target sequence that are adjacent to the matched test sub-fragment can be made. If the other test sub-fragments are located in the target sequence adjacent to the matched test sub-fragment with a total of at most E errors, then the fragment can be determined to match the target sequence. Because the non-matching test sub-fragments are compared to only portions of the target sequence that are proximate to the matching test sub-fragment, this analysis has a reduced computational complexity.

To enhance the first matching operation that detects "perfect" matches between test sub-fragments and the sequence, an index of sub-sequences within the target sequence may be constructed. Test sub-fragments can be compared with the entries in this index quickly and efficiently to determine if they match any of the entries. Of course, storing the index will be disk-intensive. However, in many cases, the benefit in terms of improved matching performance with respect to very large numbers of fragments may justify the cost of storage used to index a finite number of sequences. For human genome testing, it is usually the case that there is only one specific complete genome that is used as the target sequence, the one generated from the most recent "build" of the genome The following description will describe systems and methods used for matching test fragments to sequences in the context of human genomic research. It will be recognized to one of skill in the art that the systems and methods described herein may also be advantageously employed in any endeavor that seeks to locate a test fragment within a target sequence with at most a number E errors.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable medium", as used herein, refers to a medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Data store", as used herein, refers to a physical and/or logical entity that can store data. A data store may be, for example, a database, a table, a file, a list, a queue, a heap, a memory, a register, and so on. In different examples, a data store may reside in one logical and/or physical entity and/or may be distributed between 2 or more logical and/or physical entities.

"Logic", as used herein, includes but is not limited to hardware, firmware, software stored as computer executable instructions on a computer-readable medium or in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

"Query", as used herein, refers to a semantic construction that facilitates gathering and processing information. A query may be formulated in a database query language (e.g., SQL (structured query language), an OQL (object query language), a natural language, and so on.

"Signal", as used herein, includes but is not limited to, electrical signals, optical signals, analog signals, digital signals, data, computer instructions, processor instructions, messages, a bit, a bit stream, or other means that can be received, transmitted and/or detected.

"Software", as used herein, includes but is not limited to, one or more executable instruction that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

FIG. 1 illustrates an example embodiment of a sequence matching system 100 that locates test fragments in a target sequence with at most a number E errors. A target sequence 105 having a length K is presented for matching with test fragments. In one example embodiment, a target sequence in the form of genomic data from a file may be loaded into a database table column having a genomic type. During the loading of genomic sequences, the existence of a genome_table table in the genome schema may be confirmed. It may also be verified that the genome_column in the genome_table refers to a column of type genomic_type.

A sequence indexing logic 110 creates an index 115 for the target sequence 105. The index 115 maps sub-sequences of the target sequence to their offset within the target sequence. Thus, the entry aaccgc corresponds to the first sub-sequence in the target sequence 105 having a length of 6 characters, the entry accgct is the second sub-sequence with an offset of one character, and so on. The length of the sub-sequences that will be index entries may be chosen to achieve a balance between storage requirements and matching performance as will be described in more detail later. The index may be constructed as a b-tree index that indexes all sub-sequences in the target sequence having the predetermined length.

The system 100 includes a fragment matching logic 125. The fragment matching logic 125 receives a test fragment 120 to be matched to the target sequence 105. The example test fragment 120 contains 2 matching errors, a gap (or surplus character) at the second character position and a mismatch at the eighth character position. The fragment matching logic 125 also receives a number of permissible matching errors E for the match. The fragment matching logic breaks the fragment 125 into E+1 test sub-fragments and determines if any of the test sub-fragments is located within the target sequence 105 with no errors. If none of the test sub-fragments match the target sequence with no errors, it has been determined that the test fragment does not match the target sequence with no more than the number E errors.

In the described embodiment, an error includes a mismatch between corresponding characters in the sub-sequence and test fragment or a gap error. A gap error occurs when a test fragment includes a surplus character that is not in the sub-sequence. In other words, a gap error occurs when the test fragment would match the sub-sequence if the surplus character were skipped or ignored. For example, if a sub-sequence (in bold) ctggaaccgtcaggtcacc (seq. ID no. 1) is compared against a test sub-fragment accgtgcaggt (seq. ID no. 2), they are considered to be a match with one gap error. This is because if the character g in position 5 (the first character is in position 0) of the test sub-fragment is ignored, there would be an exact match. The same test sub-fragment will also match a sub-sequence gacttacgtgcaggtgt (seq. ID no. 3) with the character c in position 2 of the sub-fragment being determined as a gap error.

If a test sub-fragment matches the target sequence 105 with no errors, the fragment matching logic 125 determines if the other test sub-fragments match portions of the target sequence 105 adjacent to the matching test sub-fragment with no more than a total of E errors. If the other test sub-fragments match with no more than E errors, the fragment matching logic outputs a match offset 130 corresponding to the starting location of the test fragment in the target sequence. The match offset 130 may also include an error offset that corresponds to the position of any mismatching characters or surplus characters (gap error) in the test fragment. When the index is a B-tree index, it may not be necessary to match every test fragment one at a time. The collection of test sub-fragments may be sorted so that the index may be merge joined with the sorted test sub-fragments.

When an index 115 is used to determine whether a test sub-fragment matches with no errors (an exact match), the length of the sub-sequence may be smaller, equal to, or larger than the length of the test sub-fragment. To account for differences in length between the sub-sequences and a test sub-fragment, in one embodiment, an exact match is detected when the first number M characters in the subsequence match the first M characters in the test sub-fragment with no errors, where M is the smaller of the length of the test sub-fragment and the sub-sequences. Once a match between the first M characters in the test sub-fragment and a sub-sequence is detected, the complete test fragment may be aligned with the target sequence such that the already discovered matching positions are aligned. After that it is a matter of checking both sides of the matching positions for exact match or for a match with errors.

It is possible for a test fragment to appear multiple times within a target sequence (with up to E errors). In one embodiment, when a test sub-fragment matches the target sequence in multiple locations, each of those matches is analyzed with the adjacent test sub-fragments for a potential match of the entire test fragment with at most E errors as follows. After the test fragment is split into test sub-fragments, all exact matches for that sub-fragment are considered one at a time. If a test sub-fragment matches a sub-sequence, its adjacent sub-fragments are then evaluated to determine if the entire test fragment matches the target sequence with at most E errors. The same analysis is performed for the other sub-fragments. This approach may return a match between a specific test fragment and a specific target sequence multiple times. This possibility of duplicate detected matches may be dealt with by including a duplicate elimination phase or by altering the matching process to avoid duplicates.

In the embodiment shown in FIG. 1, the fragment matching logic 125 accesses the index 115 to determine if any test sub-fragments match the target sequence with no errors. However, in other embodiments, the fragment matching logic 125 determines if test sub-fragments match with no errors using some other technique. In these embodiments the system does not include a sequence indexing logic. In other embodiments, the fragment matching logic accesses an index that was created by components outside of the system 100. In these embodiments, the system does not include a sequence indexing logic.

Figure 2:
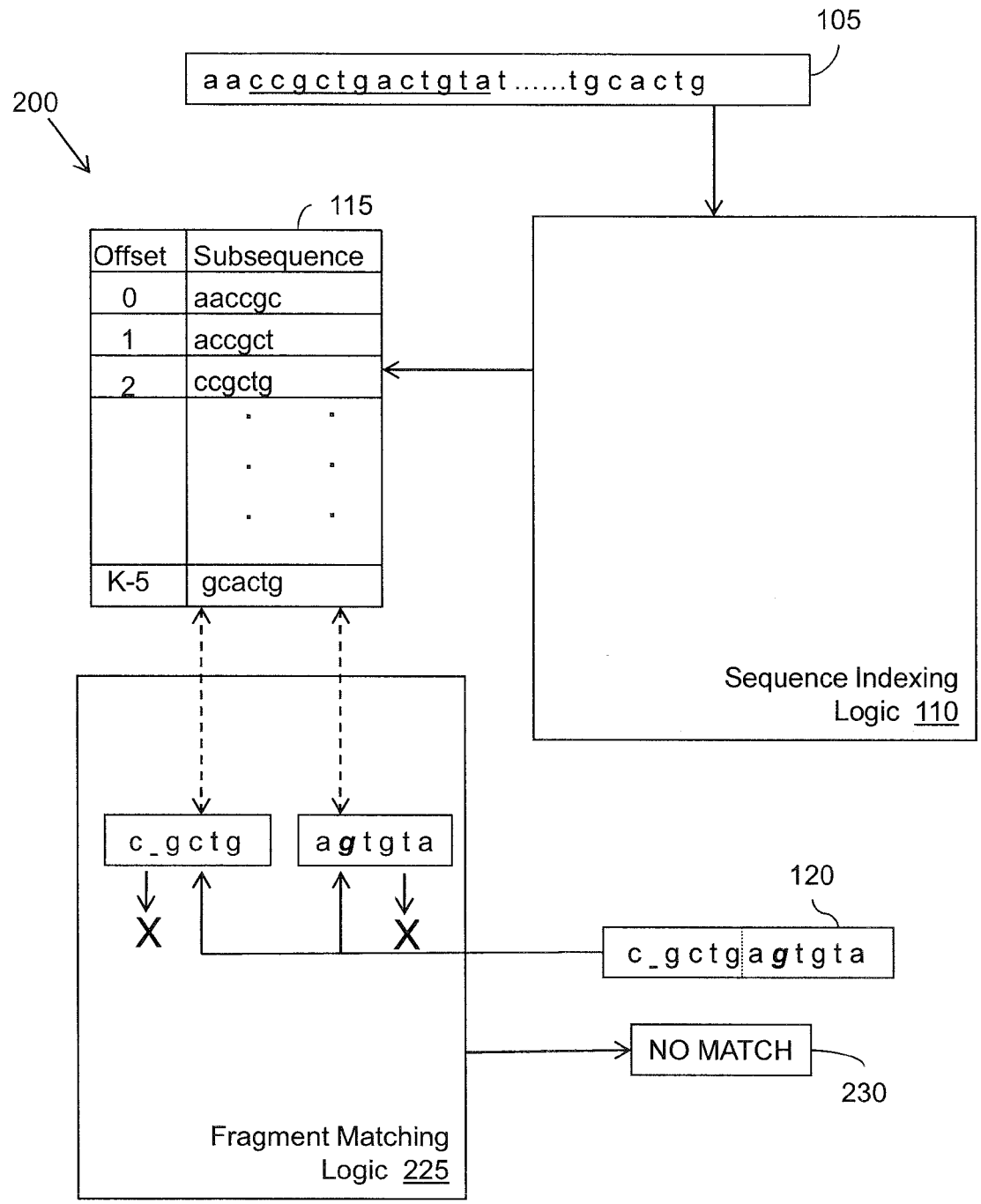
FIG. 2 illustrates another example embodiment of a system associated with sequence matching allowing for errors, where block 105 represents seq. ID no. 4, and where block 120 represents seq. ID no. 5.

FIG. 2 illustrates an example embodiment of a sequence matching system 200 that matches test fragments such as the example test fragment 120 to the target sequence 105 with no more than one error (E=1). In this embodiment, the index 115 indexes sub-sequences having a length of 6 characters. This length may be chosen to achieve a balance between storage requirements and matching performance, as will be described later. A fragment matching logic 225 divides the test fragment 120 into E+1, or 2, test sub-fragments each having a length of 6 characters. The fragment matching logic compares these fragments to the entries in the index 115 and determines that neither fragment matches with no errors. An output 230 that indicates that no match was found is produced by the fragment matching logic 225.

Figure 3:
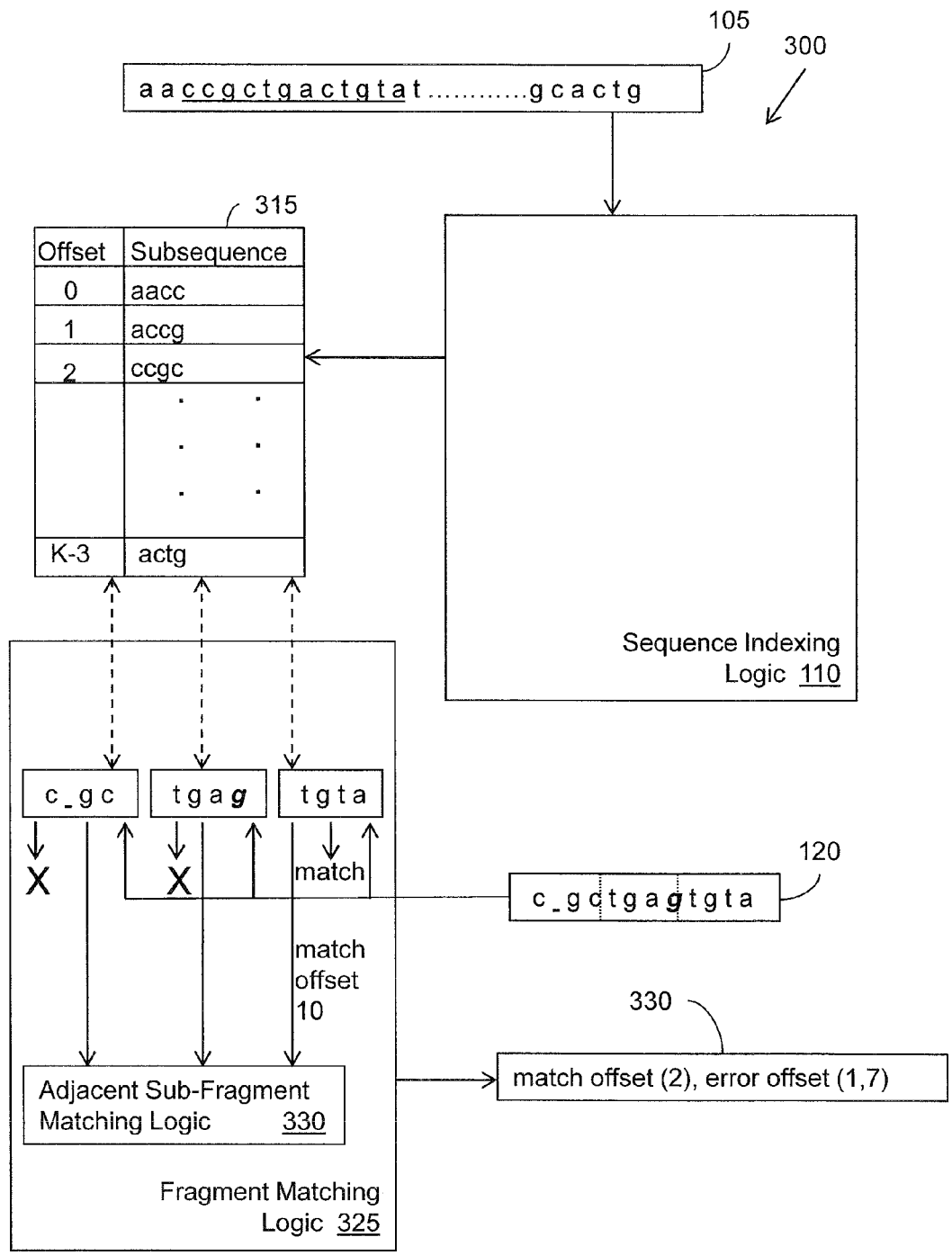
FIG. 3 illustrates another example embodiment of a system associated with sequence matching allowing for errors, where block 105 represents seq. ID no. 4, and where block 120 represents seq. ID no. 5.

FIG. 3 illustrates an example embodiment of a sequence matching system 300 that matches test fragments such as the example test fragment 120 to the target sequence 105 with at most 2 errors (E=2). The same index 115 use in FIGS. 1 and 2 is used for the embodiment described in FIG. 3. A fragment matching logic 325 will divide the 12 character test fragment 120 into E+1, or 3, test sub-fragments each having a length of 4 characters. The fragment matching logic compares these fragments to the entries in the index 115 and determines that the right-most test sub-fragment matches an entry in the index.

The offset of this matching portion (offset=10) is passed to an adjacent test sub-fragment matching logic 330 that determines if the other 2 test sub-fragments match portions of the target sequence adjacent to the matching test sub-fragment. The adjacent test sub-fragment matching logic 330 uses the passed match offset to determine what portions of the target sequence to match. In the example illustrated in FIG. 3, it is determined that the 2 other test sub-fragments match with a total of only 2 errors. A match offset 330 is output by the fragment matching logic 325 that identifies an offset within the target sequence where the matching test fragment is located. The match offset 330 also includes the offsets within the test fragment of the 2 errors.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
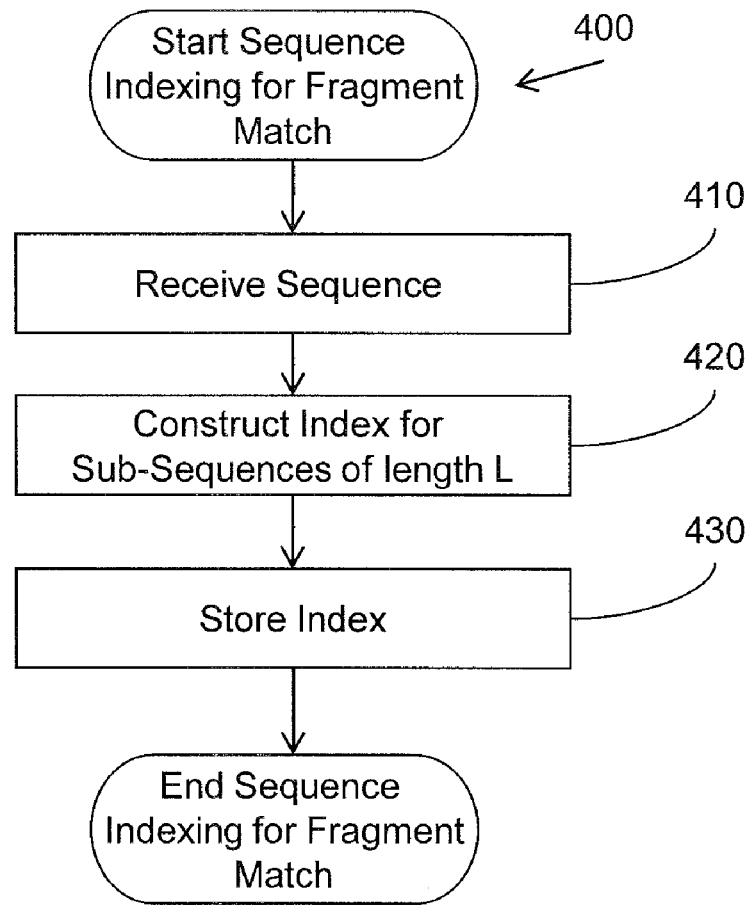
FIG. 4 illustrates an example embodiment of a method associated with sequence matching allowing for errors.

FIG. 4 illustrates an example embodiment of a method 400 that indexes a target sequence for use in fragment matching. At 410 the target sequence to indexed is received. At 420, an index is constructed for sub-sequences of the target sequence having a length L. At 430 the index is stored for use in test fragment matching.

The sub-sequence length L may be chosen to achieve a balance between storage requirements and matching performance. The following discussion of example considerations for selecting a sub-sequence length will be in the context of genomic sequences. Of course, analogous considerations may be considered in other areas of biological research. Given a 4 character alphabet, a sub-sequence having a length of 16 or more will be expected to appear no more than once in a totally random sequence of 3 billion characters. This is because $4^{16}$ is greater than 3 billion. Of course, genomic sequences are not entirely random. Hence, for index entries, it may be desirable to select a sub-sequence length greater than 16 characters, such as 17-20, to reduce the number of sub-fragment matches that are not matches relative to the test fragments being matched. A sub-sequence length of between 25-30 characters may be adequate in the area of genomic research since a multi-billion ($4^{16}$ or $4^{17}$) length random sequence will have only a minute probability of actually matching a sub-fragment of size 25 or greater. For example, a length of 30 characters might be chosen to significantly reduce the number of test sub-fragment matches that do not indicate a test fragment match and thereby improve performance.

When choosing a sub-sequence length, memory consumption may also be considered in addition to performance. For a sequence having 3 billion characters, there will be almost 3 billion index entries, each of size proportional to the length of the sub-sequence. Thus for memory consumption considerations, sub-sequence lengths much greater than 40 may not be advisable.

Figure 5:
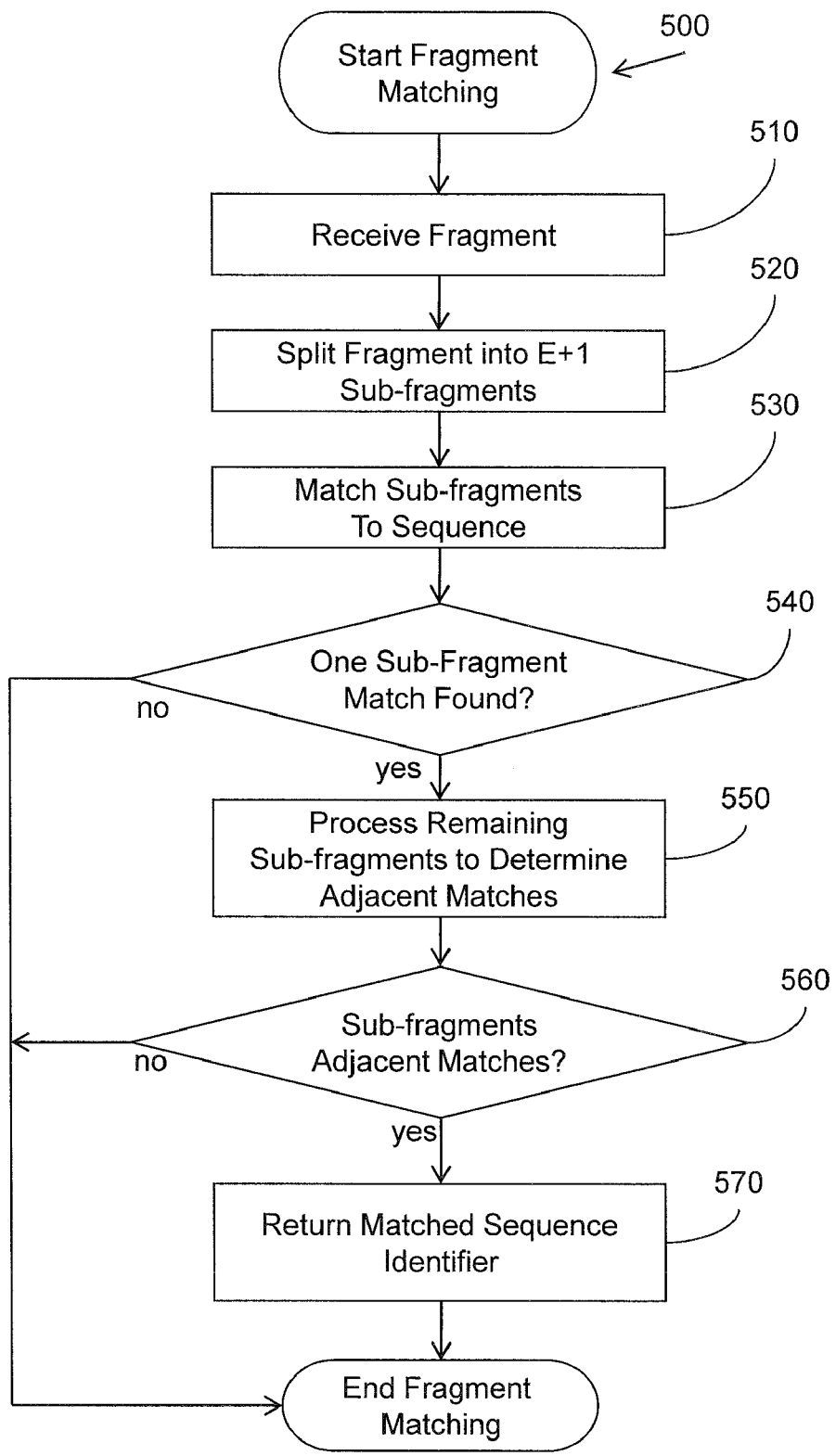
FIG. 5 illustrates another example embodiment of a method associated with sequence matching allowing for errors.

FIG. 5 illustrates an example embodiment of a method 500 that matches test fragments to a target sequence with at most E errors. At 510, the fragment is received. At 520 the fragment is split into E+1 test sub-fragments. At 530 the test sub-fragments are matched to the target sequence to determine if any of the test sub-fragments match the target sequence with zero errors. In one example embodiment, this determination may be made by accessing an index of sub-sequences in the target sequence. At 540 if a matching sub-sequence is not found, the fragment does not match with no more than E errors and the method ends.

If a matching test sub-fragment is found, at 550 the remaining test sub-fragments are processed to determine if they are located within the target sequence adjacent to the matching test sub-fragment with at most E errors. At 560 if the test sub-fragments match the target sequence in locations adjacent the matching test sub-fragment, a matched target sequence identifier that specifies the location of the test fragment within the target sequence is returned at 570. If the test sub-fragments do not match the target sequence in locations adjacent the matching test sub-fragment, the test fragment is determined not to match the target sequence in the location of the sub-sequence under consideration. If the entire target sequence has not been checked for matches with the test sub-fragments, at 580 the method loops back to search for additional matches. The method thus outputs zero or more matches of the test fragment with the target sequence.

While FIGS. 3 and 4 illustrate various actions occurring in serial, it is to be appreciated that various actions illustrated in FIGS. 3 and 4 could occur substantially in parallel. By way of illustration, a first process could compare test sub-fragments to the target sequence for a perfect match, a second process could process non-matching test sub-fragments in the event that one test sub-fragment is a perfect match with the sequence, and a third process could return the results of matching. While three processes are described, it is to be appreciated that a greater and/or lesser number of processes could be employed and that lightweight processes, regular processes, threads, and other approaches could be employed.

In one example, methods described herein may be implemented as computer executable instructions. Thus, in one example, a computer-readable medium may store computer executable instructions that if executed by a machine (e.g., processor) cause the machine to perform a method that includes receiving a test fragment to be located within a target sequence with at most a number E errors; breaking the test fragment into E+1 test sub-fragments; determining if one test sub-fragment is located within the target sequence with no errors; if one test sub-fragment is located within the target sequence with no errors, determining if the other test sub-fragments are located within the target sequence adjacent to the test sub-fragment with at most E errors; and if the other test sub-fragments are located within the target sequence adjacent the test sub-fragment with at most E errors, returning a location of the test fragment within the sequence.

While executable instructions associated with the above method are described as being stored on a computer-readable medium, it is to be appreciated that executable instructions associated with other example methods described herein may also be stored on a computer-readable medium.

Figure 6:
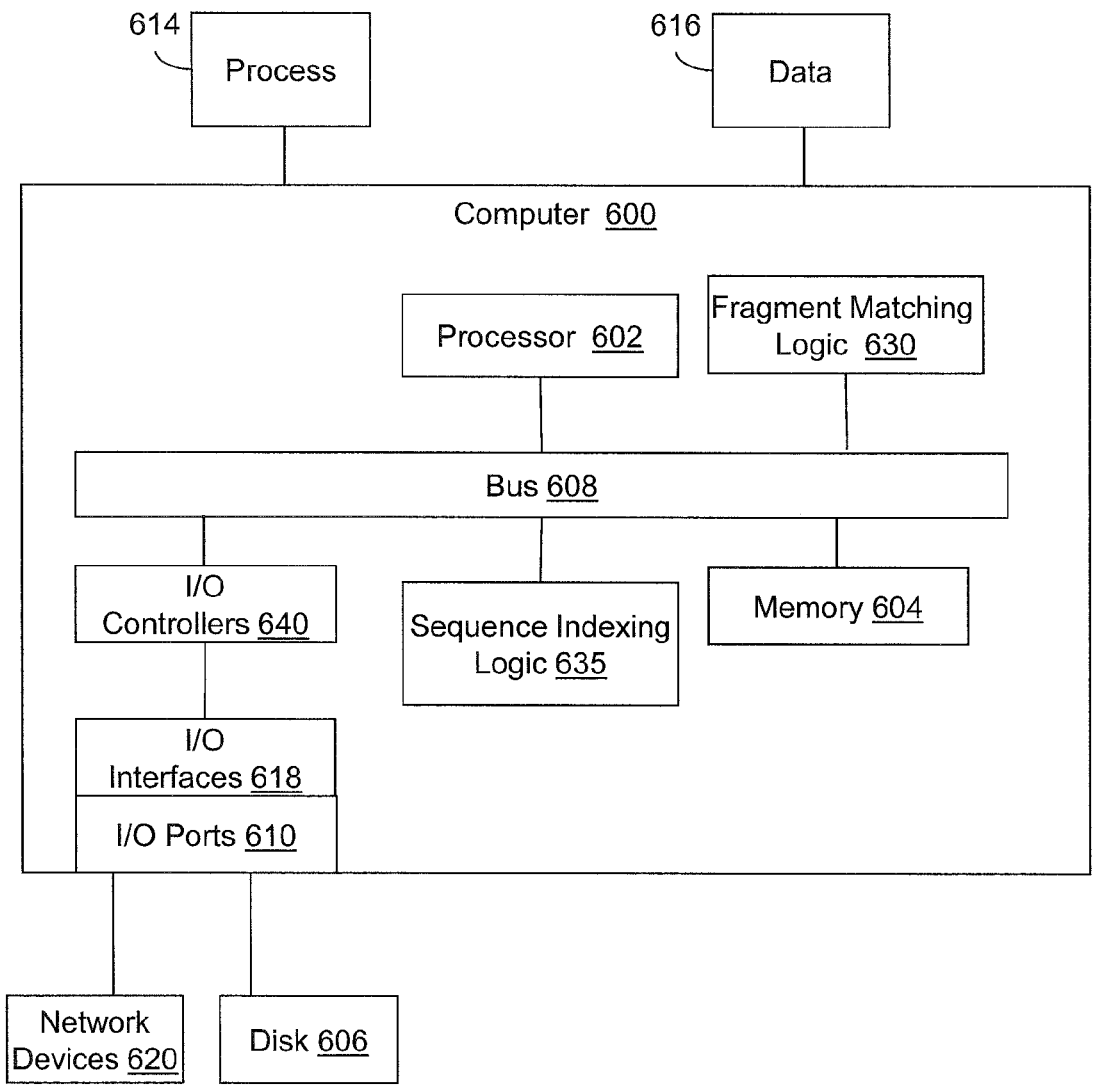
FIG. 6 illustrates an example computing environment in which example systems and methods, and equivalents, may operate.

FIG. 6 illustrates an example computing device in which example systems and methods described herein, and equivalents, may operate. The example computing device may be a computer 600 that includes a processor 602, a memory 604, and input/output ports 610 operably connected by a bus 608. In one example, the computer 600 may include a fragment matching logic 630 configured to facilitate sequence matching allowing for errors. In different examples, the logic 630 may be implemented in hardware, software stored as computer executable instructions on a computer-readable medium, firmware, and/or combinations thereof. While the logic 630 is illustrated as a hardware component attached to the bus 608, it is to be appreciated that in one example, the logic 630 could be implemented in the processor 602.

Thus, logic 630 may provide means (e.g., hardware, firmware) for receiving a test fragment to be located within a target sequence with at most a number E errors and means (e.g., hardware, firmware) for breaking the test fragment into E+1 test sub-fragments;

Logic 630 may also provide and means (e.g., hardware, firmware) for determining if one test sub-fragment is located within the target sequence with no errors. If one test sub-fragments is located within the target sequence with no errors, the means for determining determines if the other test sub-fragments are located within the target sequence adjacent to the one test sub-fragment with at most E errors. If the other test sub-fragments are located within the target sequence adjacent the one test sub-fragment with at most E errors, the means for determining returns a location of the test fragment within the target sequence. The means may be implemented, for example, as an ASIC (application specific integrated circuit) programmed to perform fragment matching. The means may also be implemented as computer executable instructions that are presented to computer 600 as data 616 that are temporarily stored in memory 604 and then executed by processor 602.

In one example the computer 600 may include a sequence indexing logic 635 configured to facilitate sequence matching allowing for errors. The logic 635 may provide means (e.g., hardware, firmware) for receiving a target sequence in which test fragments are to be located with no more than a number E errors and means (e.g., hardware, firmware) for indexing consecutive sub-sequences of the sequence, where the sub-sequences have a length that is selected to achieve a balance between storage requirements and matching performance. The logic 635 may also provide means (e.g., hardware, firmware) for storing the resulting index for use in locating test fragments in the sequence.

Generally describing an example configuration of the computer 600, the processor 602 may be a variety of various processors including dual microprocessor and other multi-processor architectures. A memory 604 may include volatile memory and/or non-volatile memory. Non-volatile memory may include, for example, ROM (read only memory), PROM (programmable ROM), and so on. Volatile memory may include, for example, RAM (random access memory), SRAM (synchronous RAM), DRAM (dynamic RAM), and so on.

A disk 606 may be operably connected to the computer 600 via, for example, an input/output interface (e.g., card, device) 618 and an input/output port 610. The disk 606 may be, for example, a magnetic disk drive, a solid state disk drive, a floppy disk drive, a tape drive, a Zip drive, a flash memory card, a memory stick, and so on. Furthermore, the disk 606 may be a CD-ROM (compact disk) drive, a CD-R (CD recordable) drive, a CD-RW (CD rewriteable) drive, a DVD (digital versatile disk and/or digital video disk) ROM, and so on. The memory 604 can store a process 614 and/or a data 616, for example. The disk 606 and/or the memory 604 can store an operating system that controls and allocates resources of the computer 600.

The bus 608 may be a single internal bus interconnect architecture and/or other bus or mesh architectures. While a single bus is illustrated, it is to be appreciated that the computer 600 may communicate with various devices, logics, and peripherals using other busses (e.g., PCI (peripheral component interconnect), PCIE (PCI express), 1394, USB (universal serial bus), Ethernet). The bus 608 can be types including, for example, a memory bus, a memory controller, a peripheral bus, an external bus, a crossbar switch, and/or a local bus.

The computer 600 may interact with input/output devices via the i/o interfaces 618 and the input/output ports 610. Input/output devices may be, for example, a keyboard, a microphone, a pointing and selection device, cameras, video cards, displays, the disk 606, the network devices 620, and so on. The input/output ports 610 may include, for example, serial ports, parallel ports, and USB ports.

The computer 600 can operate in a network environment and thus may be connected to the network devices 620 via the i/o interfaces 618, and/or the i/o ports 610. Through the network devices 620, the computer 600 may interact with a network. Through the network, the computer 600 may be logically connected to remote computers. Networks with which the computer 600 may interact include, but are not limited to, a LAN (local area network), a WAN (wide area network), and other networks.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: This sequence was generated by selecting random
      characters. The sequence was created for use in explaining operation of a sequence matching algorithm and is not intended to
represent a real genomic sequence.

<400> SEQUENCE: 1
ctggaaccgt caggtcacc                                                        19

<210> SEQ ID NO 2
<211> LENGTH: 11
<212> TYPE: DNA
<213> ORGANISM: Artificial Sequence
<220> FEATURE:
<223> OTHER INFORMATION: This sequence was generated by selecting random
      characters.  The sequence was created for use in explaining
      operation of a sequence matching algorithm and is not intended to
      represent a real genomic sequence.

<400> SEQUENCE: 2
accgtgcagg t                                                                11

<210> SEQ ID NO 3
<211> LENGTH: 17
<212> TYPE: DNA
<213> ORGANISM: Artificial Sequence
<220> FEATURE:
<223> OTHER INFORMATION: This sequence was generated by selecting random
      characters.  The sequence was created for use in explaining
      operation of a sequence matching algorithm and is not intended to
      represent a real genomic sequence.

<400> SEQUENCE: 3
gacttacgtg caggtgt                                                          17

<210> SEQ ID NO 4
<211> LENGTH: 15
<212> TYPE: DNA
<213> ORGANISM: Artificial Sequence
<220> FEATURE:
<223> OTHER INFORMATION: This sequence was generated by selecting random
      characters.  The sequence was created for use in explaining
      operation of a sequence matching algorithm and is not intended to
      represent a real genomic sequence.

<400> SEQUENCE: 4
aaccgctgac tgtat                                                            15

<210> SEQ ID NO 5
<211> LENGTH: 10
<212> TYPE: DNA
<213> ORGANISM: Artificial Sequence
<220> FEATURE:
<223> OTHER INFORMATION: This sequence was generated by selecting random
      characters.  The sequence was used to show operation of a matching
      algorithm, and is not intended to represent a real genomic
      sequence

<400> SEQUENCE: 5
gctgagtgta                                                                  10

What is claimed is:

1. A non-transitory computer-readable medium storing computer executable instructions that when executed by a computer cause the computer to perform a method, the method comprising:
   receiving a test fragment to be located within a target sequence with at most a number E errors;
   breaking the test fragment into E+1 test sub-fragments;
   determining if one test sub-fragment is located within the target sequence with no errors;
   if one test sub-fragment is located within the target sequence with no errors, determining if the other test sub-fragments are located within the target sequence adjacent to the test sub-fragment with a total of at most E errors; and
   if the other test sub-fragments are located within the target sequence adjacent the test sub-fragment with a total of at most E errors, returning a location of the test fragment within the sequence.

2. The non-transitory computer-readable medium of claim 1 where the determining if one of the test sub-fragments is located within the target sequence with no errors is performed by accessing an index on the target sequence that indexes sub-sequences of the target sequence to an offset within the target sequence corresponding to the location of the sub-sequence.

3. The non-transitory computer-readable medium of claim 2 where the determining if one of the test sub-fragments is located within the target sequence is performed by sorting the test fragments and performing a merge join between the index and the sorted test fragments.

4. The non-transitory computer-readable medium of claim 1 comprising returning an offset within the test fragment of errors.

5. The non-transitory computer-readable medium of claim 1 where the target sequence is a sequence of letters representing genetic data.

6. The non-transitory computer-readable medium claim 1 where an error comprises a mismatch between a character in the test sub-fragment and a corresponding character in the sequence.

7. The non-transitory computer-readable medium of claim 1 where an error comprises a gap error that comprises a character in the test sub-fragment that must be ignored so that the remaining characters in the test sub-fragment match corresponding characters in the sequence.

8. The non-transitory computer-readable medium of claim 1 where determining if the other test sub-fragments are located within the target sequence adjacent to the test sub-fragment with a total of at most E errors is performed by aligning the complete test fragment with the target sequence such that the already discovered matching positions are aligned and checking both sides of the matching positions for exact match or for a match with at most E errors.

9. A non-transitory computer-readable medium storing computer executable instructions that when executed by a computer cause the computer to perform a method, the method comprising:
   receiving a target sequence within which test fragments are to be located with no more than a number E errors;
   indexing consecutive sub-sequences of the sequence, where the sub-sequences have a length that is selected to achieve a balance between storage requirements and matching performance;
   storing the resulting index for use in locating test fragments within the sequence.

10. The non-transitory computer-readable medium of claim 9 where the indexing includes mapping a sub-sequence to an offset within the target sequence corresponding to the location of the sub-sequence within the target sequence.

11. The non-transitory computer-readable medium of claim 9 comprising constructing a b tree index of consecutive sub-sequences of the target sequence.

12. A computing system, comprising:
   a processor;
   a memory;
   an interface to connect an index and a set of logics, the index and the set of logics including:
   the index of a sub-sequences from a target sequence in which test fragments are to be located with at most a number E errors;
   a fragment matching logic configured to receive a test fragment to be located within the target sequence with at most a number E errors; to break the test fragment into E+1 test sub-fragments; to access the index to determine if one test sub-fragment is located within the target sequence with no errors; the fragment matching logic comprising an adjacent test sub-fragment matching logic to determine if the other test sub-fragments are located within the target sequence adjacent to the one test sub-fragment with a total of at most E errors if the fragment matching logic determines that one test sub-fragment is located within the target sequence with no errors; and
   where the fragment matching logic is configured to return a location of the test fragment within the target sequence if the adjacent test sub-fragment matching logic determines that the other test sub-fragments are located within the target sequence adjacent the one test sub-fragment with a total of at most E errors.

13. The computing system of claim 12 comprising a sequence indexing logic that constructs the index of sub-sequences.

14. The computing system of claim 13 where the sequence indexing logic constructs a b-tree index that indexes all sub-sequences within the target sequence having a predetermined length.

15. The computing system of claim 14 where the predetermined length is selected to achieve a balance between storage requirements and matching performance.

16. A computer-implemented method comprising:
   receiving a target sequence against which test fragments are to be matched with no more than a number E errors;
   indexing consecutive sub-sequences of the sequence;
   receiving a test fragment to be located within the target sequence with at most the number E errors;
   breaking the test fragment into E+1 test sub-fragments;
   determining if one test sub-fragment is located within the target sequence with no errors;
   if one test sub-fragments is located within the target sequence with no errors, determining if the other test sub-fragments are located within the target sequence adjacent to the one test sub-fragment with at most E errors; and
   if the other test sub-fragments are located within the target sequence adjacent the one test sub-fragment with at most E errors, returning a location of the test fragment within the sequence
   wherein the steps above are performed on a computer.

17. The computer-implemented method of claim 16 where the indexing includes mapping all sub-sequences in the target sequence having a predetermined length to an offset within the target sequence corresponding to the location of the sub-sequence within the sequence.

18. The computer-implemented method of claim 16 where the target sequence is a sequence of letters representing genetic data.

19. The computer-implemented method of claim 16 where an error comprises a mismatch between a character in the test sub-fragment and a corresponding character in the sequence.

20. The computer-implemented method of claim 16 where an error comprises a gap error that comprises a character in the test sub-fragment that must be ignored so that the remaining characters in the test sub-fragment match corresponding characters in the sequence.

\* \* \* \* \*

UNITED STATES PATENT AND TRADEMARK OFFICE
CERTIFICATE OF CORRECTION

PATENT NO. : 8,340,917 B2
APPLICATION NO. : 12/634118
DATED : December 25, 2012
INVENTOR(S) : Banerjee et al.

It is certified that error appears in the above-identified patent and that said Letters Patent is hereby corrected as shown below:

In the Specifications:

In column 3, line 20, delete "genome" and insert -- genome. --, therefor.

In column 9, line 7, delete "sub-fragments;" and insert -- sub-fragments. --, therefor.

In the Claims:

In column 13, line 19, in Claim 6, delete "medium claim" and insert -- medium of claim --, therefor.

In column 13, line 53, in Claim 11, delete "a b tree" and insert -- a b-tree --, therefor.

Signed and Sealed this
Sixteenth Day of April, 2013

Teresa Stanek Rea
*Acting Director of the United States Patent and Trademark Office*